(12) United States Patent
Barry (10) Patent No.: US 11,110,263 B2
(45) Date of Patent: Sep. 7, 2021

(54) MAGNETIC FIXATION APPARATUS FOR PERCUTANEOUS CATHETER

(71) Applicant: Abiomed, Inc., Danvers, MA (US)

(72) Inventor: Vincent Barry, Rowley, MA (US)

(73) Assignee: ABIOMED, INC., Danvers, MA (US)

( * ) Notice: Subject to any disclaimer, the term of this patent is extended or adjusted under 35 U.S.C. 154(b) by 193 days.

(21) Appl. No.: 16/274,546

(22) Filed: Feb. 13, 2019

(65) Prior Publication Data
US 2019/0224390 A1 Jul. 25, 2019

Related U.S. Application Data

(63) Continuation of application No. 15/095,932, filed on Apr. 11, 2016, now Pat. No. 10,238,782.

(51) Int. Cl.
| | |
|---|---|
| *A61M 60/20* | (2021.01) |
| *A61M 60/205* | (2021.01) |
| *A61M 25/04* | (2006.01) |
| *A61M 60/135* | (2021.01) |

(52) U.S. Cl.
CPC .......... *A61M 60/205* (2021.01); *A61M 25/04* (2013.01); *A61M 60/135* (2021.01)

(58) Field of Classification Search
CPC .... A61M 1/1012; A61M 25/04; A61M 1/122; A61M 60/205; A61M 60/135
See application file for complete search history.

(56) References Cited

U.S. PATENT DOCUMENTS

| | | | |
|---|---|---|---|
| 4,809,713 A * | 3/1989 | Grayzel | A61N 1/057 607/116 |
| 5,944,023 A | 8/1999 | Johnson et al. | |
| 6,292,678 B1 | 9/2001 | Hall et al. | |
| 7,974,678 B2 | 7/2011 | Maschke | |
| 10,238,782 B2 * | 3/2019 | Barry | A61M 25/04 |
| 2008/0006281 A1 | 1/2008 | Sih et al. | |
| 2015/0196752 A1 | 7/2015 | Bunch et al. | |

* cited by examiner

*Primary Examiner* — Amber R Stiles
(74) *Attorney, Agent, or Firm* — Botos Churchill IP Law LLP (57) ABSTRACT

A catheter apparatus can include a first magnet coupled to a catheter and a second magnet configured to couple to a patient's skin. When the catheter and the first magnet are positioned within a patient's body, the second magnet can exert a magnetic force on the first magnet that stabilizes the catheter relative to the second magnet. The second magnet can be directly attached to the patient's skin or secondary devices such as straps can be used to place the second magnet in a fixed position relative to the patient's body. In some implementations, a plurality of magnets can facilitate holding the catheter in a substantially fixed position within the patient.

3 Claims, 9 Drawing Sheets

MAGNETIC FIXATION APPARATUS FOR PERCUTANEOUS CATHETER

CROSS-REFERENCE TO RELATED APPLICATIONS

This application is a continuation of U.S. application Ser. No. 15/095,932, filed Apr. 11, 2016 (now allowed). The disclosure of the foregoing application is hereby incorporated by reference in its entirety.

BACKGROUND

Percutaneous catheters are inserted into the vascular system of a patient as part of numerous therapeutic and diagnostic procedures. For example, a percutaneous mechanical circulatory support device, also commonly referred to as a heart pump, can be introduced into the vascular system of a patient through the femoral artery and inserted into the heart (e.g., the left ventricle) to pump blood from the heart into a blood vessel (e.g., the aorta). This pumping action can assist the natural cardiac pump function or replace the natural cardiac pump function. Percutaneous catheters may also be used for other procedures such as angioplasty, electrophysiology study, and ablation.

It is often desirable to fix a percutaneous catheter at a particular location within a patient. In the more specific case of a heart pump, for example, it is desirable for the pump to remain fixed in place in a position that optimizes the flow of blood from the heart and into the blood vessel. If the heart pump strays too far in or out from this optimal position in the heart, reduced flow and/or other complications may arise. For example, when the pump is positioned too far in the left ventricle such that the inlet and the outlet port(s) are both within the ventricle, the device can cause blood to circulate within the left ventricle rather than being delivered into the ascending aorta, thereby decreasing the support provided to the patient. Additionally, if the outlet port(s) of the heart pump moves it may be blocked by leaflets of a valve (e.g., the aortic valve). Blood delivered by the heart pump may impinge on the valve, which can cause lysing of blood cells or hemolysis due to shear stress. When the device is in such a position, the valve may also interfere with the flow of blood through the device, decreasing the support provided to the patient.

It may be desirable for a percutaneous catheter to remain in a patient for a long period of time, such as for a patient who requires long-term assistance with cardiac pumping. However, when a percutaneous catheter remains in a patient for a long period of time, it can be more difficult to maintain the position of the percutaneous catheter in the patient. Movement of the patient can cause the percutaneous catheter to stray from its desired position. For percutaneous catheters that are inserted into the heart of a patient, the normal pulsatility of the heart can cause the catheter to stray from its desired position and this can require user intervention.

One solution for maintaining the position of a percutaneous catheter is to reduce slack in the catheter to reduce the possibility of movement. Another solution for maintaining the position of a percutaneous catheter inserted into the heart is a flexible atraumatic extension that extends from the distal end of the catheter. This extension may reduce the possibility of the percutaneous catheter slipping too far from its optimal position into the heart. However, other solutions would be desirable in addition to or instead of these mechanisms. Additionally, it may be desirable to fix the orientation of the catheter within the body of the patient to optimize system performance.

SUMMARY

Disclosed herein are apparatuses and methods for magnetically fixating, anchoring, or stabilizing a percutaneous catheter, for example, in long-term heart assist settings. A first magnet is coupled to the percutaneous catheter and a second magnet is coupled to the patient (or other stable structure) and substantially fixed in position and orientation. For example, the second magnet may be enclosed in a patch fixed to the patient's skin, for example by adhesive. The first and second magnets exert an attractive magnetic force on each other. The attractive magnetic force will cause little change in the position of the second magnet because the second magnet is substantially fixed in position to the patient or other stable structure. The first magnet will be drawn by the attractive magnetic force to the second magnet. As the first magnet is drawn to the second magnet, the first magnet will draw the catheter to which it is coupled along with it. At a certain position relative to the second magnet, external forces (e.g., the opposing force of the patient's internal tissue) will prevent the first magnet and the catheter from moving further towards the second magnet. In the absence of other external forces, the first magnet and catheter will remain substantially fixed at that position.

If the first and second magnets are each sufficiently elongate, the first and second magnets may be used to cause the catheter to assume a preferred orientation within a plane (e.g., the coronal plane) of the patient. The length of the second magnet may allow the second magnet to be attached to the skin of the patient within the coronal plane of the patient at a pre-determined angle relative to the patient's longitudinal axis. Similarly, the length of the first magnet may allow the first magnet to be attached to the catheter at a pre-determined angle relative to the longitudinal axis of the catheter. Upon insertion of the catheter and the first magnet into the vasculature of the patient, the north and south poles of the first magnet and the south and north poles of the second magnet, respectively, may align. The pre-determined angles of the first and second magnets can be chosen such that upon alignment of the poles of the first and second magnets, the catheter assumes a certain angle relative to the patient's longitudinal axis within the patient's coronal plane. This can allow the catheter to be fixed in a preferred orientation relative to the patient's heart, blood vessels, and other surrounding anatomical features. Since the optimal catheter orientation can vary from patient to patient, the preferred orientation can be determined based on the anatomies of multiple individuals (e.g., >20 individuals, >50 individuals, >100 individuals, >500 individuals, or any other suitable number) with different characteristics (e.g., ages, sizes, genders, etc.). The preferred catheter orientation can be selected to accommodate a certain percentage of patient anatomies (e.g., 80%, 90%, 95%, or any other suitable percentage) of the anatomies of the analyzed individuals. In some implementations, the first magnet includes a first group of two or more spatially separated magnets, and the second magnet includes a second group of two or more spatially separated magnets. In such implementations, torque can be applied to the catheter (e.g., in the coronal plane) by simultaneously applying oppositely direct forces to two magnets in the first group of magnets using the second group of magnets. This can also allow the catheter to be fixed in a preferred orientation relative to the patient's heart, blood vessels, and other surrounding anatomical features.

Substantially fixating the position and/or orientation of the catheter can improve the effectiveness of the therapeutic and/or diagnostic procedures to which the catheter is directed. For example, substantially fixating a percutaneous catheter configured as a heart pump in its optimal position and/or orientation within the heart can improve cardiac assistance. Substantially fixating the position and orientation of the catheter may be especially beneficial for therapeutic or diagnostic procedures requiring a catheter to remain in a patient's vasculature for a long period of time, because the catheter would be less likely to stray from its optimal position and orientation during a long-term procedure.

In one aspect, a catheter apparatus comprises a first magnet coupled to a catheter and a second magnet configured to couple to a patient (e.g., to the patient's skin). The second magnet exerts a magnetic force on the first magnet that stabilizes the catheter relative to the second magnet when the catheter and the first magnet are positioned inside of the patient's body.

In some implementations, the second magnet is sized to be supported by the patient's body. In certain implementations, the second magnet includes an adhesive coating configured to fix the second magnet to the patient's skin. In some implementations, the second magnet is enclosed within a patch that is configured to couple to the patient's skin.

In some implementations, the first magnet is coated with an anti-corrosive layer, compound, or material. In certain implementations, the catheter apparatus further comprises a heart pump coupled to a distal end portion of the catheter. The first magnet may be positioned proximal or distal relative to the heart pump. In some implementations, the catheter further comprises a distal portion and the first magnet is coupled to the distal portion.

In certain implementations, the surface area of the first magnet facing the patient's skin is approximately equal to 25 square millimeters. In some implementations, the surface area of the second magnet in contact with the patient's skin is approximately equal to 25 square millimeters. In certain implementations, the attractive force generated by the first and second magnets is about 2.5 N. In some implementations, the first magnet and the second magnet each have a north and south pole, and the first magnet is coupled to the catheter at a predetermined position and with a predetermined orientation such that the catheter assumes a preferred orientation relative to the patient.

In another aspect, a method for percutaneously inserting a catheter into a patient comprises inserting a catheter into the patient's vasculature, the catheter having a first magnet, and positioning a second magnet in a fixed position relative to the patient such that the first and second magnets are aligned and exert a force on each other, thereby stabilizing the position of the catheter relative to the second magnet.

In some implementations, positioning the second magnet in a fixed position relative to the patient comprises attaching the second magnet to the patient's skin with adhesive. In certain implementations the second magnet is included within a patch and the patch is directly attached to the patient's skin.

In some implementations, the first magnet is coupled to a distal portion of the catheter. In certain implementations, the catheter further comprises a heart pump disposed at an end portion of the catheter, and the first magnet is coupled to a distal end portion of the heart pump.

In some implementations, the magnetic force between the first and second magnets is about 2.5 N. In certain implementations, the first magnet and the second magnet each have a north and south pole, and the first magnet is coupled to the catheter at a predetermined position and with a predetermined orientation relative to the catheter such that the catheter assumes a preferred orientation relative to the patient.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION

To provide an overall understanding of the apparatuses and methods for magnetically fixating a percutaneously inserted catheter, certain illustrative embodiments will be described. Although the embodiments and features described herein are specifically described for use in connection with percutaneously inserted catheters, it will be understood that all the components and other features outlined below may be combined with one another in any suitable manner and may be adapted and applied to other types of therapeutic and diagnostic devices and methods.

The apparatuses and methods described herein provide an apparatus for magnetically fixating, anchoring, and/or stabilizing a percutaneous catheter using magnets. For example, the percutaneous catheter includes a first magnet that is coupled to, attached to, fixed to, or positioned on the catheter and a second magnet that is coupled to, attached to, fixed to, or positioned on the patient in a substantially fixed position and orientation. For example, the second magnet may be enclosed in a patch that is fixed to the patient's skin, such as by adhesive. The first and second magnets exert an attractive magnetic force on each other. The attractive magnetic force will cause little to no change in the position of the second magnet because the second magnet is substantially fixed in position, while the first magnet will be drawn by the attractive magnetic force to the second magnet. As the first magnet moves toward the second magnet, the first magnet will also move the catheter to which it is coupled along with it. At a certain relative position between the first magnet and the second magnet, external forces (e.g., the opposing force of the patient's internal tissue) will prevent the first magnet and the catheter from moving further towards the second magnet. In the absence of other external forces, the first magnet and the catheter will remain substantially fixed at that position.

In some implementations, the second magnet is elongate (e.g., 1 mm, 2.5 mm, 5 mm, 7.5 mm, 10 mm, 50 mm, 10 cm, 30 cm, >30 cm long). The length of the second magnet allows the second magnet to be attached to the skin of the patient within the coronal plane of the patient at a pre-determined angle relative to the patient's longitudinal axis. Similarly, the first magnet may be elongate (e.g., 1 mm, 2.5 mm, 5 mm, 7.5 mm, 10 mm, 50 mm, 10 cm, 30 cm, >30 cm long). The length of the first magnet allows the first magnet to be attached to the catheter at a pre-determined angle relative to the longitudinal axis of the catheter. Upon insertion of the catheter and the first magnet into the vasculature of the patient, the north and south poles of the first magnet and the south and north poles of the second magnet, respectively, may align. The pre-determined angles of the first and second magnets can be chosen such that upon alignment of the poles of the first and second magnets, the catheter assumes a certain angle relative to the patient's longitudinal axis within the patient's coronal plane. This can allow the catheter to be fixed in a preferred orientation relative to the patient's heart, blood vessels, and other surrounding anatomical features. In some implementations, the first magnet includes a first group of two or more spatially separated magnets, and the second magnet includes a second group of two or more spatially separated magnets. In such implementations, torque can be applied to the catheter (e.g., in the coronal plane) by simultaneously applying oppositely direct forces to two magnets in the first group of magnets using the second group of magnets. This can also allow the catheter to be fixed in a preferred orientation relative to the patient's heart, blood vessels, and other surrounding anatomical features.

Substantially fixating a percutaneous catheter configured as a heart pump in its optimal position and orientation within the heart can improve cardiac assistance. Substantially fixating the position and orientation of the catheter may be beneficial for long-term procedures, because the catheter would be less likely to stray from its optimal position and orientation during the long-term procedure.

Figure 1:
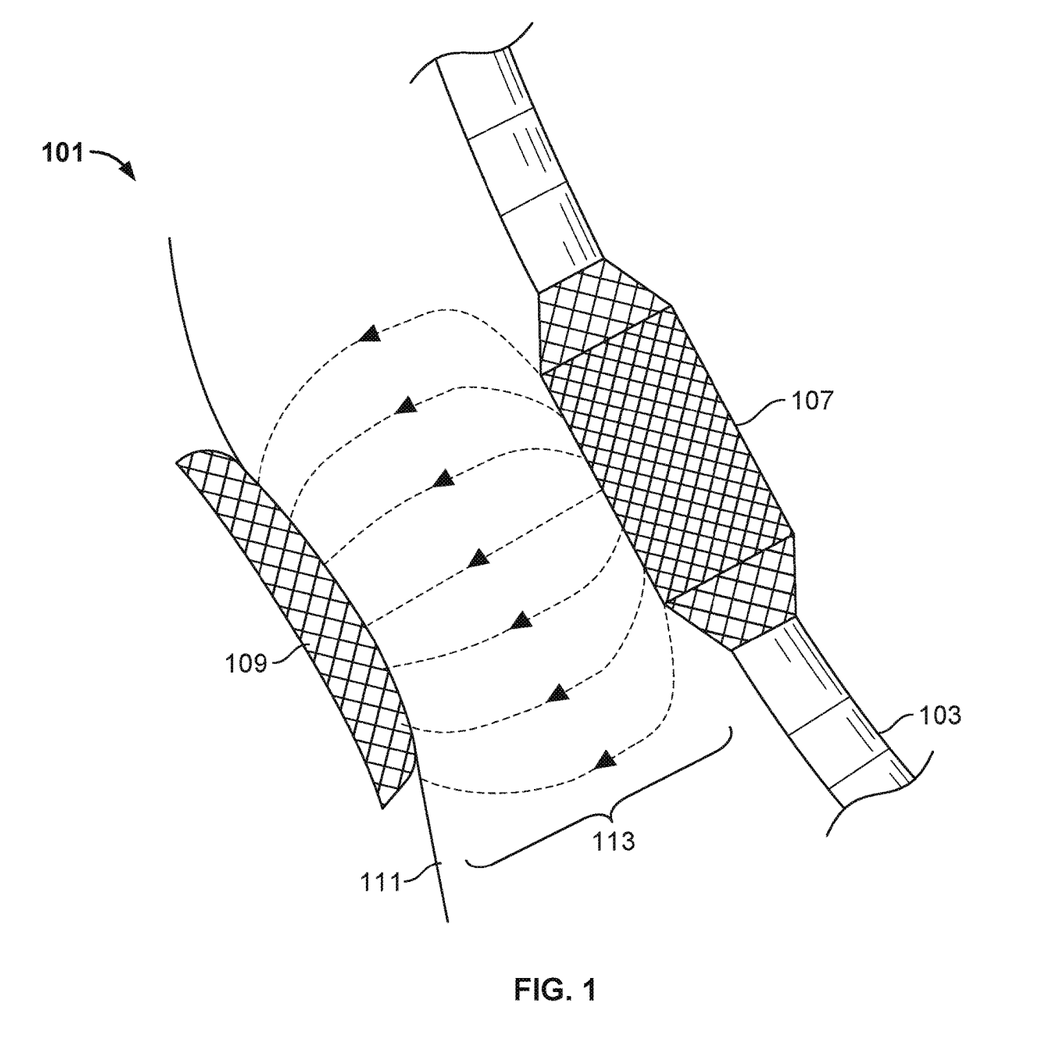
FIG. 1 shows an apparatus for magnetically fixating a percutaneously inserted catheter according to certain implementations.

FIG. 1 shows an apparatus 101 for magnetically fixating a percutaneously inserted catheter according to certain implementations. The apparatus 101 includes a catheter 103, a first magnet 107, and a second magnet 109. The first magnet 107 is coupled to the catheter 103. The second magnet 109 is coupled to the patient 111 (e.g., directly attached to the patient's skin). The first magnet 107 and the second magnet 109 exert an attractive magnetic force 113 (e.g., through the skin and tissue) on each other. The attractive magnetic force 113 will cause little change in the position of the second magnet 109 because the second magnet 109 is substantially fixed in position. The first magnet 107 will be drawn by the attractive magnetic force 113 to the second magnet 109. As the first magnet 107 moves toward the second magnet 109, the first magnet 107 will move the catheter 103 to which it is coupled along with it. At a certain position relative to the second magnet 109, external forces (e.g., the opposing force of the patient's internal tissue) will prevent the first magnet 107 and the catheter 103 from moving further towards the second magnet 109, thereby leaving the two magnets in a stable position relative to each other. In the absence of other external forces, the first magnet 107 and the catheter 103 will remain substantially fixed at that position.

Substantially fixating the position and/or orientation of the catheter 103 can improve cardiac assistance because the catheter 103 is more likely to remain at an optimal position and orientation. In particular, fixating the catheter 103 can prevent a blood inlet of the blood pump from suctioning against the wall of the heart which could cause blockage of the blood flow. Additionally, fixating the catheter 103 can prevent the blood outlet from being positioned too close to a feature of the patient's anatomy (e.g., the aortic valve) which could cause the exiting blood to experience relatively high shear stress and hemolysis. Furthermore, fixating the catheter 103 can prevent the blood outlet from being positioned in the same heart chamber as the blood inlet, which could cause recirculation of blood within the same heart chamber without substantially improving cardiac output.

The attractive magnetic force 113 generated using the apparatus 101 can be estimated using the Gilbert Model for calculating the force between magnetized surfaces:

$$F=(B_n^2 \cdot A)/(2 \cdot \mu_0)$$

where F is the magnetic force, $B_n$ is the flux density, A is the surface area, and to is the permeability of space, which equals $4\pi \times 10^{-7}$ T·m/A. In the example of FIG. 1, the magnetic field due to the first magnet 107 and the second magnet 109 can be about $B_n$=0.5 T. Additionally, an appropriate size of the surface area of the magnets facing or contacting the patient's skin is about A=25 mm². Therefore, the magnetic force of attraction generated is about 2.5 N. In some implementations, the magnetic force is more than 2.5 N (e.g., 3 N, 5 N, 10 N, >10 N). In certain implementations, the magnetic force is less than 2.5 N (e.g., 2 N, 1 N, 0.5 N, 0.1 N, <0.1 N).

Figure 2:
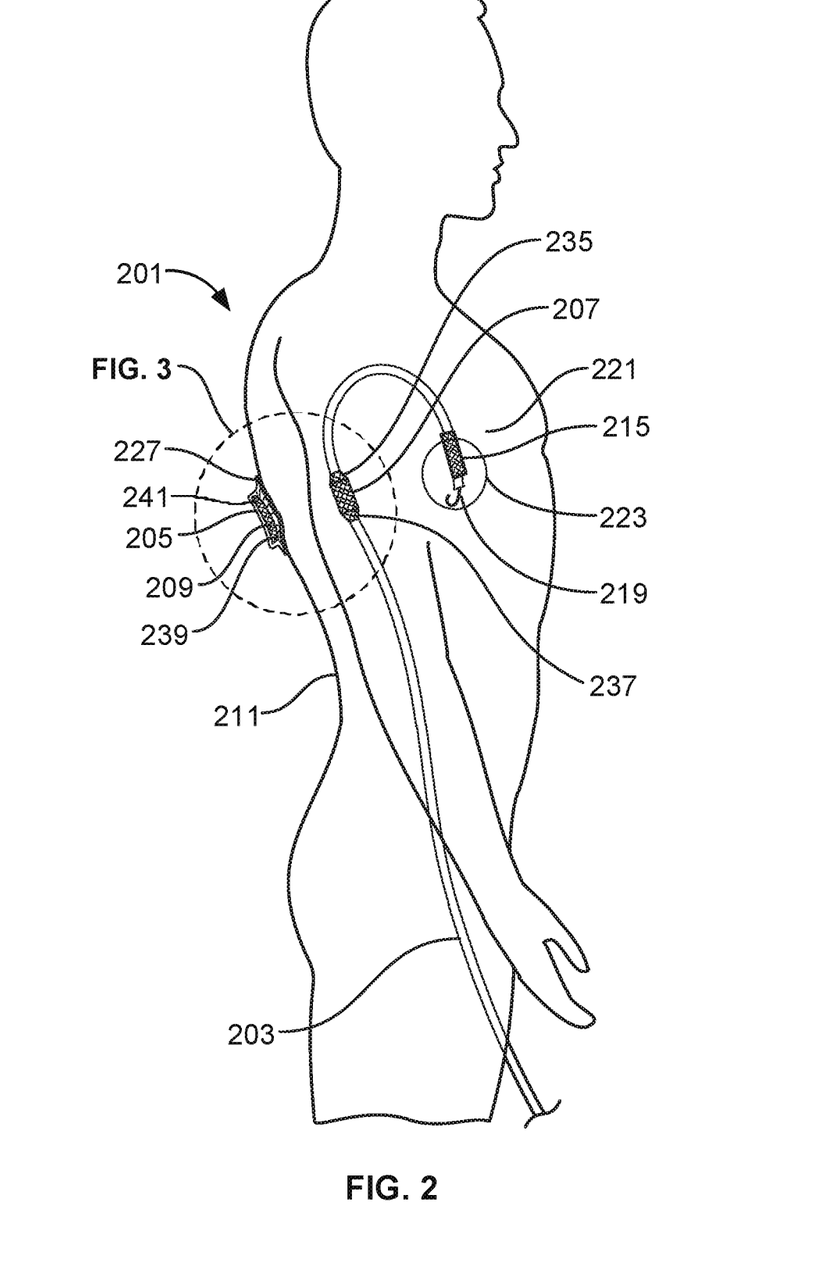
FIG. 2 is a side view of a patient and an apparatus for magnetically fixating a percutaneously inserted catheter according to certain implementations.
Figure 3:
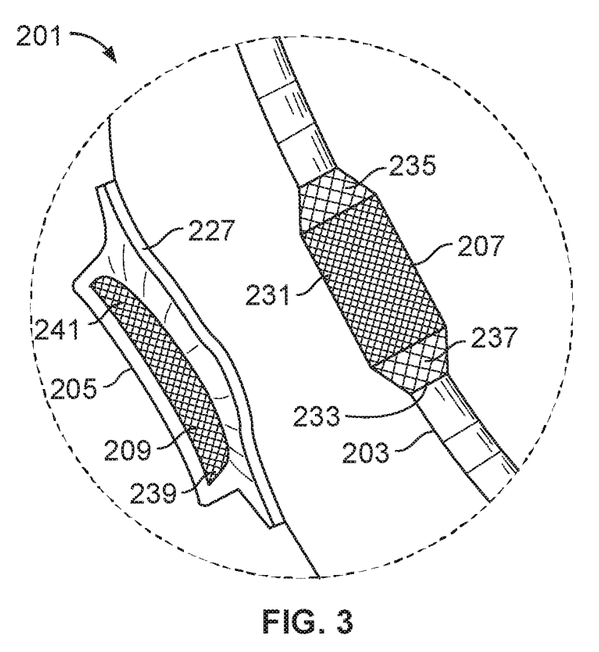
FIG. 3 is a magnified view of the apparatus of FIG. 2.

FIG. 2 is a side view of a patient and an apparatus 201 for magnetically fixating a percutaneously inserted catheter according to certain implementations. FIG. 3 is a magnified view of the apparatus of FIG. 2. The apparatus 201 includes a catheter 203, a first magnet 207, a second magnet 209, and a patch 205. The catheter 203 is configured as a heart pump. In certain implementations, the catheter 203 may be any other suitable type of percutaneously inserted catheter (for example, configured for procedures such as angioplasty, electrophysiology study, or ablation). As shown, the catheter 203 includes a heart pump 215 at an end portion 221 of the catheter 203. The first magnet 207 is coupled to the catheter 203 and the second magnet 209 is enclosed in the patch 205. The patch 205 is coupled to the skin of a patient 211 by adhesive 227 coated on the surface of the patch 205.

The catheter 203 may be inserted into a patient's vasculature at various access points, such as through an artery for left heart support or through a vein for right heart support. For example, in FIG. 2 the catheter 203 is inserted into the femoral artery (not shown) in the leg of the patient 211. The catheter 203 is passed through the vasculature of the patient 211 until the end portion 221 of the catheter 203 reaches its destination. In FIG. 2, the end portion 221 is positioned in the left ventricle of the heart 223 of the patient 211 and extends across the aortic valve into the aorta. In some implementations, the distal portion 221 is positioned entirely or partially within the left ventricle, the right ventricle, the atria, the aorta, the pulmonary vein, or any other suitable location.

The end portion 221 includes a heart pump 215 for pumping blood from a chamber of the heart 223 (e.g., the left ventricle) into a blood vessel of the patient 211 (e.g., the aorta). This pumping action may assist the natural cardiac pumping function or replace the natural cardiac pumping function. The heart pump 215 includes a drive shaft (which may be driven by a motor within the heart pump 215 or external to the heart pump 215), one or more impeller blades driven by the drive shaft, a blood inlet, and a blood outlet. Rotation of the impeller blades draws blood from a chamber of the heart 223 into the heart pump 215 through one or more windows in the blood inlet and out of the heart pump 215 through one or more windows in the blood outlet to a blood vessel. In the example of FIG. 2, the catheter 203 includes a flexible atraumatic extension 219 (e.g., a pigtail) at its distal end to reduce the possibility of the catheter 203 slipping too far from its optimal position into the heart 223 of the patient 211.

The first magnet 207 of the catheter can vary in any number of ways. As shown, the first magnet 207 is attached to the catheter 203. The first magnet 207 can be coupled to the catheter 203 in various ways, such as by a fixture, an interference fit, an interlocking connection, adhesive, fasteners, straps, or any other suitable coupling means. The first magnet 207 can have various shapes and configurations. As shown, the first magnet 207 is generally tubular and has an outer surface 231 and a bore 233 through which the catheter 203 extends. While a tubular first magnet 207 is shown, in some implementations the first magnet 207 is cubical, spherical, cylindrical, toroidal, or any other suitable shape. The first magnet has a north pole 235 and a south pole 237. Additionally, the first magnet 207 may be any type of magnet. For example, the first magnet 207 may be a permanent magnet or may be comprised of a soft magnetic material, such as an iron-chromium-aluminium (FeCrAl) alloy (e.g., KANTHAL® manufactured by Sandvik). In some implementations, the surface area of the first magnet 207 facing the patient's skin may be approximately 25 mm$^2$ or less. For other examples, the surface area of the first magnet 207 facing the patient's skin may be 20 mm$^2$, 15 mm$^2$, 10 mm$^2$, 5 mm$^2$, <5 mm$^2$, or any other appropriate surface area. In some implementations, the surface area of the first magnet 207 facing the patient's skin may be greater than 25 mm$^2$. For other examples, the surface area of the first magnet 207 facing the patient's skin may be 30 mm$^2$, 40 mm$^2$, 50 mm$^2$, >50 mm$^2$, or any other appropriate surface area.

In implementations where the first magnet 207 is a rare earth magnet, it is preferable to coat, encase, enclose, or hermetically seal the first magnet 207 with a layer, compound, or material (e.g., coated or encased with a biocompatible material/biocompatible metallic material such as stainless steel, aluminum, gold, platinum, etc.) to reduce corrosion, because rare earth magnets may corrode in the bloodstream of the patient 211.

In FIG. 2, the first magnet 207 is coupled to the catheter 203 proximal to the heart pump 215 and is located at the approximate height of the heart 223 of the patient 211. Although the first magnet 207 is depicted in this location, the first magnet 207 may be coupled to the catheter 203 at any suitable location along the length of the catheter 203. For example, the first magnet 207 may be coupled to the flexible atraumatic extension 219, to a distal end portion/cannula of the heart pump 215, to the catheter 203 distal to the heart pump 215, or to the catheter 203 proximal to the heart pump 215 and located at the approximate height of the abdomen of the patient 211. The location of the first magnet 207 relative to the body of the patient 211 is preferably determined by the location along the catheter 203 at which the first magnet 207 is coupled to the catheter 203 and how far into the patient's vasculature the catheter 203 is inserted.

The position of the first magnet 207 relative to the motor of the heart pump 215 is an important consideration. The magnetic field generated by the first magnet 207 may interfere with the performance of the motor of the heart pump 215 if the first magnet 207 and the motor of the heart pump 215 are positioned too close to each other. Distances that may be too close include 1 mm, 5 mm, 1 cm, 2 cm, 3 cm, 4 cm, 5 cm, 10 cm, 15 cm, >15 cm, or other distances. This is especially important when the heart pump 215 is too small to accommodate a yoke, magnetic amplifier, or magnetic reflux jacket around the motor that could serve as a barrier to external magnetic fields. For example, the heart pump 215 may be too small to accommodate a yoke when the heart pump 215 has an outer diameter of 12 Fr (4 mm) to 14 Fr (4.67 mm). When the heart pump 215 is physically large (e.g., 21 Fr (7 mm) in diameter), it can accommodate a large yoke, magnetic amplifier, or magnetic reflux jacket which can serve as a barrier to external magnetic fields. With a heart pump 215 having a large yoke, magnetic amplifier, or magnetic reflux jacket, positioning of the first magnet 207 relative to the motor of the heart pump 215 can be less critical. The position of the first magnet 207 relative to the heart pump 215 can also determine if a portion of the heart pump 215 is drawn to a wall of a heart chamber. If the first magnet 207 is located nearby the heart pump 215, the attraction of the second magnet 209 may pull the heart pump 215 against a wall of the heart 223. If the portion of the heart pump 215 containing the blood inlet becomes stuck against the wall of the heart 223, the inlet may be blocked, thus impeding cardiac assistance. If the portion of the heart pump 215 containing the blood outlet becomes stuck against the wall of the heart 223, the exiting blood may experience relatively high shear stress, thereby causing hemolysis. To reduce the risk of both problems, it may be preferable to space the first magnet 207 from the heart pump 215 by an appropriate distance (e.g., 1 mm, 5 mm, 1 cm, 2 cm, 3 cm, 4 cm, 5 cm, 10 cm, 15 cm, >15 cm, or any other suitable distance).

The second magnet 209 can have various shapes and configurations. As shown, the second magnet 209 is substantially flat. In some implementations, the second magnet 209 is disk-shaped, cubical, spherical, cylindrical, toroidal, box-shaped, planar, or any other appropriate shape. The second magnet 209 has a north pole 239 and a south pole 241. The second magnet 209 may be any suitable type of magnet. For example, the second magnet 209 may be a permanent magnet or may be comprised of a soft magnetic material, such as an iron-chromium-aluminium (FeCrAl) alloy (e.g., KANTHAL® manufactured by Sandvik). In some implementations, the surface area of the second magnet 209 in contact with the patient's skin may be approximately 25 mm$^2$ or less. For other examples, the surface area of the second magnet 209 in contact with the patient's skin may be 20 mm$^2$, 15 mm$^2$, 10 mm$^2$, 5 mm$^2$, <5 mm$^2$, or any other appropriate surface area. In some implementations, the surface area of the second magnet 209 in contact with the patient's skin may be greater than 25 mm$^2$. For other examples, the surface area of the second magnet 209 in contact with the patient's skin may be 30 mm², 40 mm², 50 mm², >50 mm², or any other appropriate surface area.

As described above, the second magnet 209 is coupled to the skin of the patient 211. In FIGS. 2-3, the second magnet 209 is enclosed within a patch 205. The patch 205 is configured to physically couple to the skin of the patient 211 in a substantially fixed position and orientation. The patch 205 may be composed of fabric, plastic, latex, or any other appropriate material. The patch 205 may be coupled to the patient 211 at various locations, or to other stable locations outside the patient. For example, in FIG. 2, the patch 205 is coupled to the upper back of the patient 211, at the approximate height of the heart 223 of the patient 211. In some implementations, the patch 205 is coupled to the lower back of the patient 211. In certain implementations, the patch 205 is coupled to the patient 211 on the upper chest of the patient 211 at the approximate height of the heart 223 of the patient 211. In some implementations, the patch 205 is coupled to the front abdomen region of the patient 211. The patch 205 is coupled to the patient 211 by an adhesive 227 coated on a surface of the patch 205.

If the first magnet 207 and the second magnet 209 are each sufficiently elongate, the first magnet 207 and the second magnet 209 may be used to cause the catheter 203 to assume a preferred orientation within a plane (e.g., the coronal plane) of the patient 211. For example, the second magnet 109 may be 1 mm, 2.5 mm, 5 mm, 7.5 mm, 10 mm, 50 mm, 10 cm, 30 cm, or >30 cm long. The length of the second magnet 209 allows the second magnet 109 to be attached to the skin of the patient within the coronal plane of the patient at a pre-determined angle relative to the patient's longitudinal axis. Similarly, the first magnet 107 may be 1 mm, 2.5 mm, 5 mm, 7.5 mm, 10 mm, 50 mm, 10 cm, 30 cm, or >30 cm long. The length of the first magnet 207 allows the first magnet 207 to be attached to the catheter 203 at a pre-determined angle relative to the longitudinal axis of the catheter 203. Upon insertion of the catheter 203 and the first magnet 207 into the vasculature of the patient 211, the north pole 235 and the south pole 237 of the first magnet 207 and the south pole 241 and the north pole 239 of the second magnet 209, respectively, align. The pre-determined angles of the first magnet 207 and the second magnet 209 can be chosen such that upon alignment of the poles of the first magnet 207 and the second magnet 209, the catheter 203 assumes a certain angle relative to the patient's longitudinal axis within the patient's coronal plane. This can allow the catheter 203 to be fixed in a preferred orientation relative to the patient's heart, blood vessels, and other surrounding anatomical features. In some implementations, the first magnet 207 includes a first group of two or more spatially separated magnets, and the second magnet 209 includes a second group of two or more spatially separated magnets. In such implementations, torque can be applied to the catheter (e.g., in the coronal plane) by simultaneously applying oppositely direct forces to two magnets in the first group of magnets using the second group of magnets. This can also allow the catheter 203 to be fixed in a preferred orientation relative to the patient's heart, blood vessels, and other surrounding anatomical features.

Substantially fixating the position and/or orientation of the catheter 203 using the apparatus 201 can improve cardiac assistance by preventing the catheter 203 from straying/moving from its desired or optimal position. Because the catheter 203 is more likely to move from its optimal position/orientation during a long-term procedure, the magnetic fixation may be especially beneficial for longer term procedures (e.g., for catheters positioned inside of a patient for >1 hr, >2 hr, >6 hr, >12 hr, >24 hr, or any other suitable length).

Figure 4:
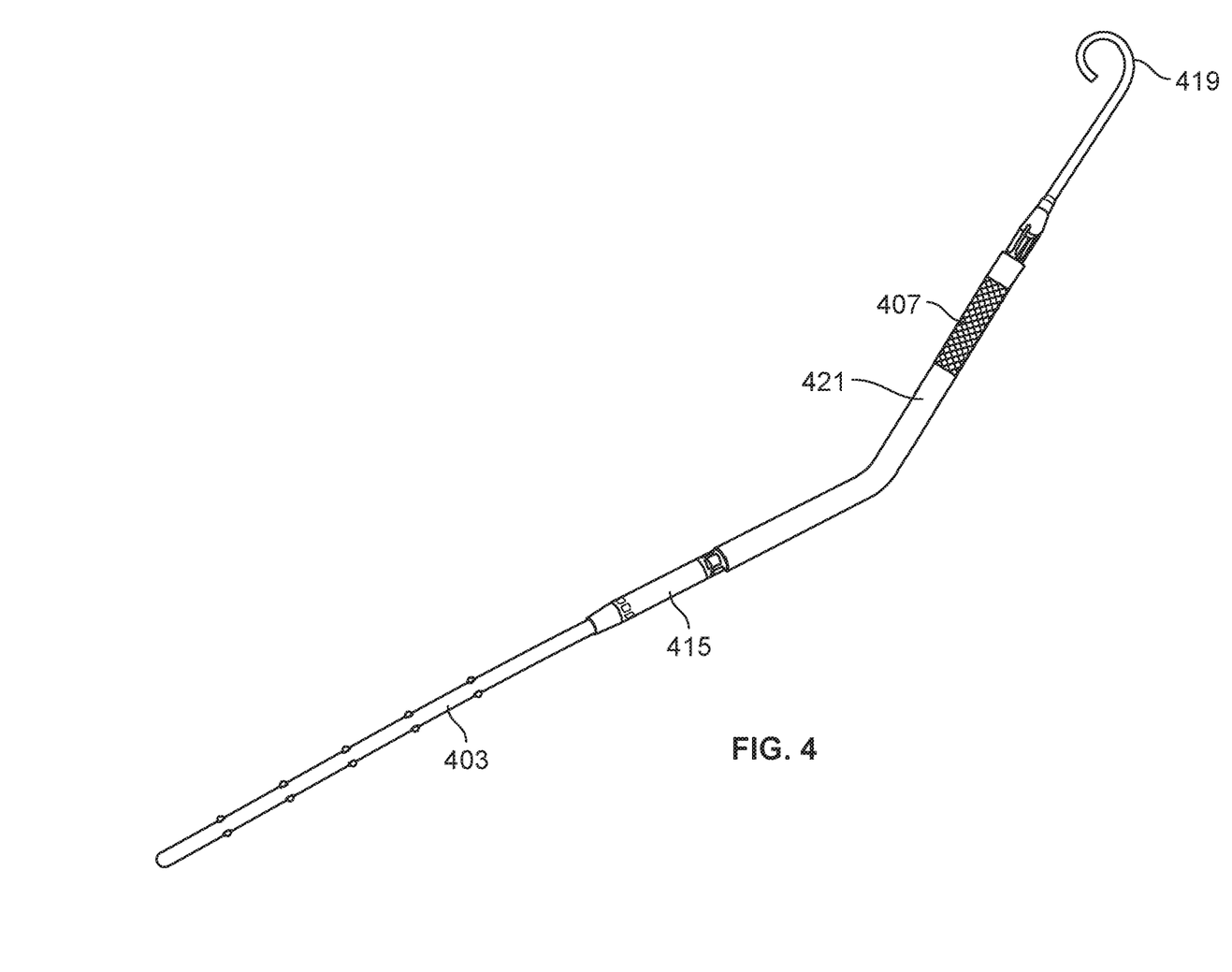
FIG. 4 shows an illustrative configuration of a catheter that includes magnetic fixation distal to its pump.

FIG. 4 shows an illustrative configuration of a catheter 403 that includes magnetic fixation distal to its pump. The catheter 403 can include any combination of features previously described. The catheter 403 shown is configured as a heart pump. The catheter 403 includes a heart pump 415, a distal portion/cannula 421, a flexible atraumatic extension 419, and a first magnet 407. The distal portion 421 can be substantially flexible and can be substantially straight in its resting state or can have at least one bend in its resting state. For example, the distal portion 421 in FIG. 4 has a single bend. As will be appreciated, the distal portion 421 and the at least one bend can be straightened during insertion (such as by advancing the distal portion 421 through a vessel and/or over a guidewire) and the distal portion 421 can have one or more bends when deployed into the heart. The one or more bends can facilitate positioning the distal portion 421 in a desired axial and rotational orientation within the heart and the one or more bends do not interfere with fluid flow therethrough. The flexible atraumatic extension 419 reduces the possibility of the catheter 403 slipping too far from its optimal position into the heart. The flexible atraumatic extension 419 may be a pigtail tip, a rounded tip, or any other suitable atraumatic feature. As shown, the first magnet 407 is coupled to the distal portion 421 of the catheter 403. This coupling may be by adhesive, fasteners, straps, or any other suitable coupling means. The first magnet 407 may have a bore through which the catheter 403 passes. In certain implementations, the first magnet 407 is coupled to the flexible atraumatic extension 419. The first magnet 407 may be coupled to a proximal end portion of the flexible atraumatic extension 419, a distal end portion of the flexible atraumatic extension 419, or in a middle portion of the flexible atraumatic extension 419. In some implementations, the first magnet 407 is coupled to a distal end portion of the heart pump 415. In certain implementations, the first magnet 407 is coupled to the catheter 403 distal to the heart pump 415. In some implementations, the first magnet 407 is coupled to the catheter 403 proximal to the heart pump 415 and is located at the approximate height of the abdomen of the patient.

Figure 5:
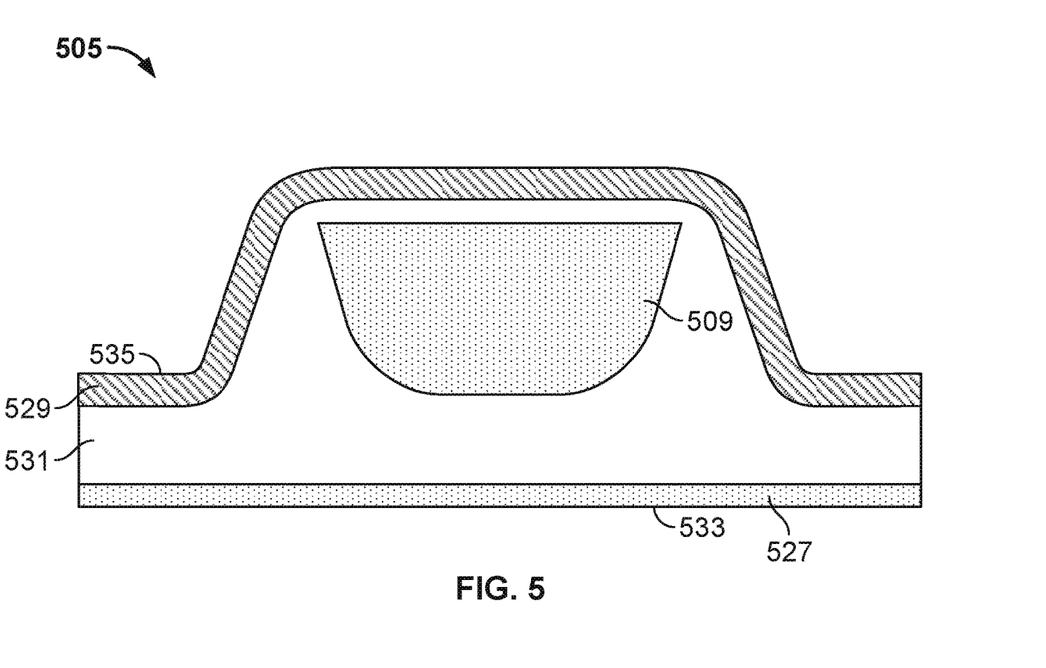
FIG. 5 is a cross-sectional view of a patch for a second magnet according to certain implementations.
Figure 6:
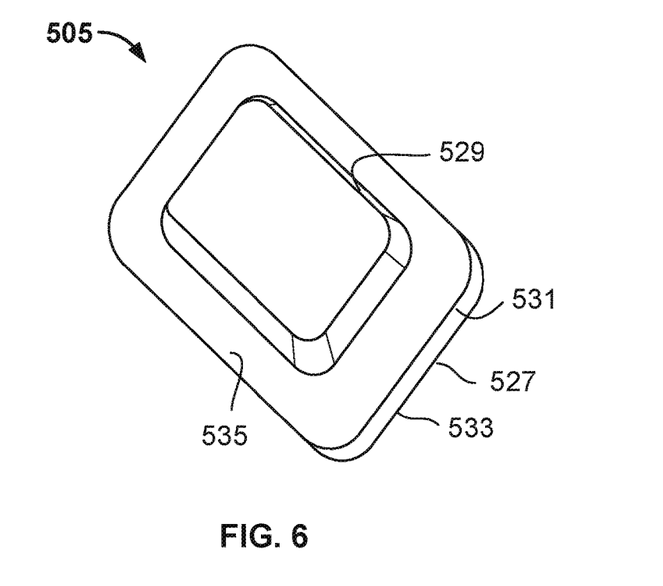
FIG. 6 is a perspective view of the patch of FIG. 5.

FIG. 5 is a cross-sectional view of a patch 505 for a second magnet 509 according to certain implementations. FIG. 6 is a perspective view of the patch 505 of FIG. 5. As shown, the patch 505 includes a first layer 529, a second layer 531, an adhesive layer 527, and the second magnet 509. The adhesive layer 527 is coated on a first outer surface 533 of the patch 505, the surface 533 configured to be coupled to a patient. The first layer 529 is on a second outer surface 535 of the patch 505. The second magnet 509 is embedded within the second layer 531. The first layer 529 and the second layer 531 may be composed of fabric, plastic, latex, or any other appropriate material. The first layer 529 and the second layer 531 may be composed of different materials than each other. For example, the second layer 531 may be composed of a material that provides better comfort against the skin of a patient, conforms better to the shape of the patient's body, and/or is better configured for enclosing the second magnet 509. The first layer 529 may be composed of a material that can protect the second layer 531 and the second magnet 509 from external disturbances (e.g., water, contact with clothing or bedding, contact with medical instruments), provide structural integrity to the second layer 531, and/or be more amenable to interacting with packaging. While the patch 505 may have various sizes, shapes, and configurations, the patch 505 is preferably small in size and light weight. The patch 505 shown is less than 10 cm×10 cm in size. In some implementations, the size of the patch 505 is <30 cm×30 cm, <20 cm×20 cm, <5 cm×5 cm, <2 cm×2 cm, <1 cm×1 cm, or any suitable size. The patch 505 shown is less than 2 cm thick. In some implementations, the thickness of the patch 505 is <5 cm, <4 cm, <3 cm, <1 cm, <0.5 cm, <1 mm, or any suitable thickness. The weight of the patch 505 shown is less than 100 g. In some implementations, the weight of the patch 505 is <1 kg, <500 gm, <50 gm, <10 gm, or any suitable weight. The patch 505 shown is rectangular in shape. In some implementations, the patch 505 is square, circular, or any other suitable shape. One skilled in the art will appreciate that other configurations and designs of the patch 505 are possible and that the patch 505 can include more or fewer layers than depicted. For example, the patch 505 may lack the first layer 529, or the patch 505 may include a third layer.

Figure 7:
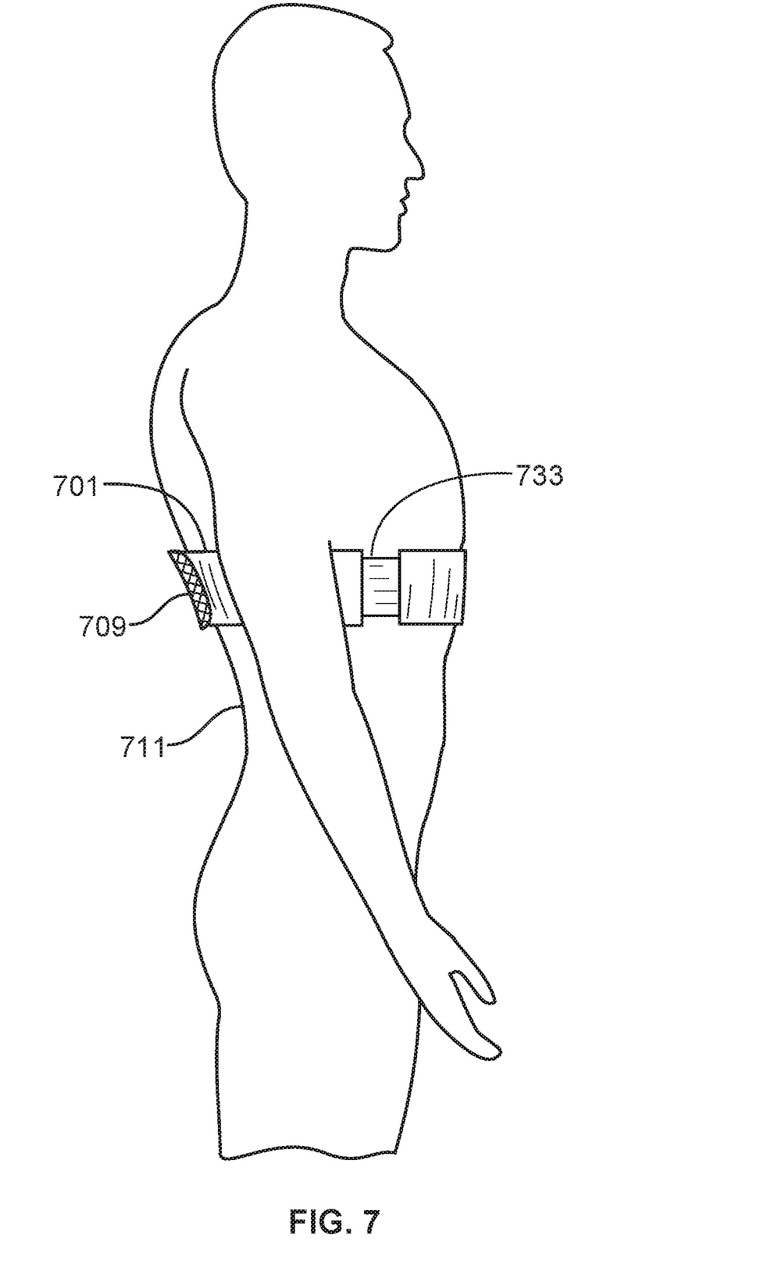
FIG. 7 shows a strap for coupling a second magnet to the skin of a patient according to certain implementations.

FIG. 7 shows a strap 701 for coupling a second magnet 709 to the skin of a patient 711 according to certain implementations. The strap 701 includes the second magnet 709 and a fastener 733. The second magnet 709 is encapsulated within the strap 701. The strap 701 wraps around a portion of the body of the patient 711, such as around the patient's chest and over or under the patient's arms, and fastens together with the fastener 733.

Other means for coupling the second magnet 709 to the patient 711 are possible. In certain implementations, the second magnet 709 is encapsulated within a band containing an elastic material that clings around a portion of the body of the patient 711. In certain implementations, the second magnet 709 is positioned directly adjacent to the skin of the patient 711 and is held in place by a bandage extending across an external surface of the second magnet 709 and adhering to the skin of the patient 711 on either side of the second magnet 709. An advantage of the latter coupling means is a specialized patch, strap, or band encapsulating a magnet may not be necessary. Additionally, the bandage can be replaced without needing to replace the magnet. Although various coupling means are discussed, persons skilled in the art will appreciate that the second magnet 709 can be affixed directly to the skin of the patient 711 by adhesive.

Figure 8:
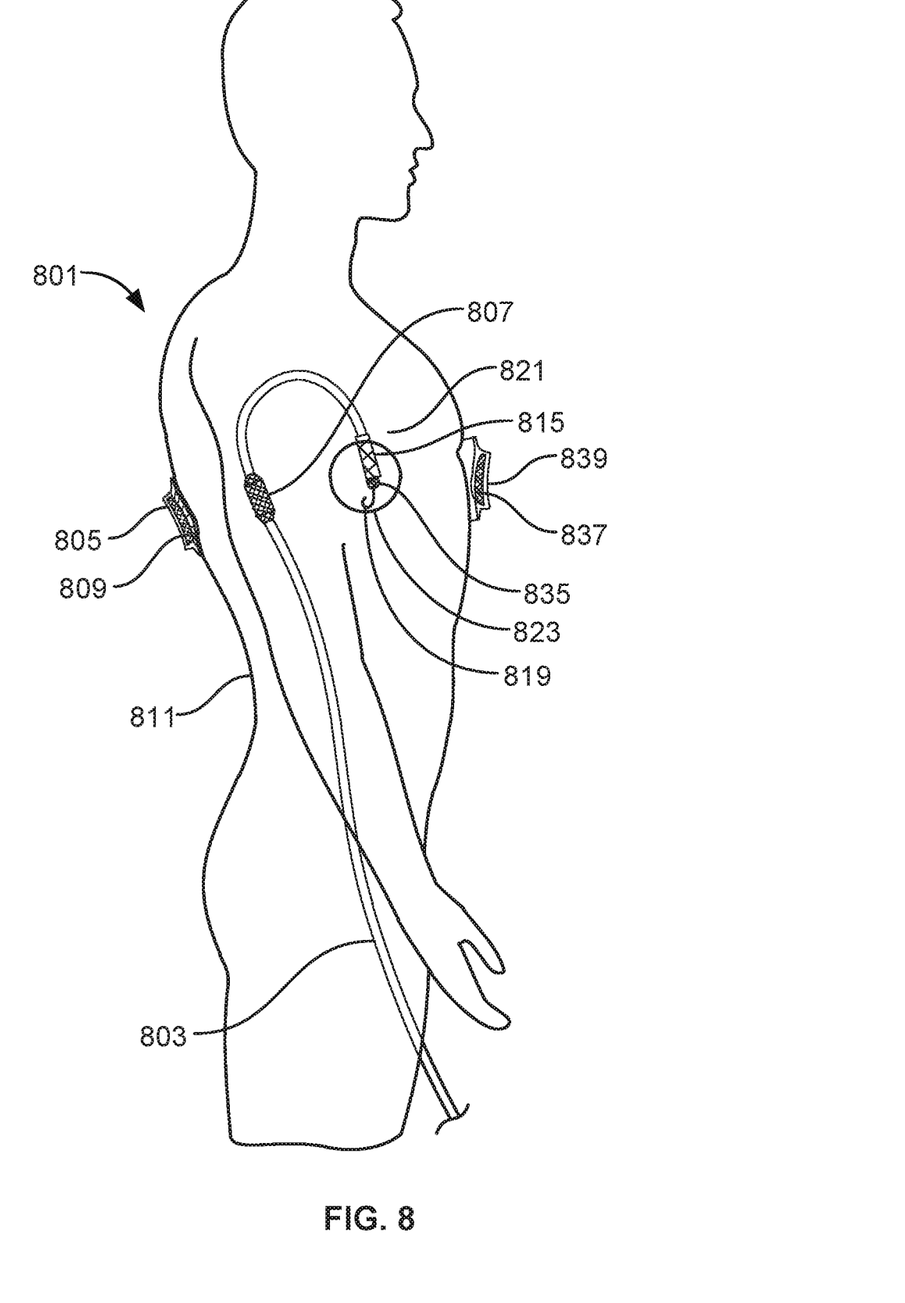
FIG. 8 shows a patient and an illustrative apparatus for magnetically fixating a percutaneously inserted catheter, the apparatus having a plurality of magnets.

A plurality of magnets can be used, for example, with any of the embodiments described above. FIG. 8 shows a patient and an illustrative apparatus 801 for magnetically fixating a percutaneously inserted catheter, the apparatus 801 having a plurality of magnets. As shown, the apparatus 801 includes a catheter 803, a first magnet 807, a second magnet 809, a third magnet 835, a fourth magnet 837, a first patch 805, and a second patch 839. The catheter 803 includes a heart pump 815, an end portion 821, and a flexible atraumatic extension 819. The flexible atraumatic extension 819 reduces the possibility of the catheter 803 slipping too far from its optimal position into the heart 823. The flexible atraumatic extension 819 may be a pigtail tip, a rounded tip, or any other suitable atraumatic structure. The first magnet 807 is coupled to the catheter 803 proximal to the heart pump 815 and is located at the approximate height of the heart 823 of a patient 811. The second magnet 809 is encapsulated in the first patch 805. The first patch 805 is coupled to the patient 811 on the upper back by adhesive on the surface of the first patch 805. The third magnet 835 is coupled to the flexible atraumatic extension 819. The fourth magnet is encapsulated in the second patch 839. The second patch 839 is coupled to the patient 811 on the upper chest by adhesive on the surface of the second patch 839. The second magnet 809 exerts an attractive magnetic force on the first magnet 807 and the fourth magnet 837 exerts an attractive magnetic force on the third magnet 835. Using these additional magnets can allow a user to precisely control the fixed position of the catheter 803, can increase how rigidly the catheter 803 is fixed in place, and/or can increase robustness to failure of one of the multiple magnets. If the first magnet 807 and the third magnet 835 are sufficiently far away from each other (for example, 75-125 mm), their magnetic fields will not interfere with each other substantially. Similarly, if the second magnet 809 and the fourth magnet 837 are sufficiently far away from each other (for example, 75-125 mm), their magnetic will not interfere with each other substantially. In some implementations, it may be desirable for the first magnet 807 and the third magnet 835 to be sufficiently close together such that their magnetic fields interact. Similarly, in some implementations, it may be desirable for the second magnet 809 and the fourth magnet 837 to be sufficiently close together such that their magnetic fields interact.

In some implementations, the second magnet 809, the fourth magnet 837, the first patch 805, and the second patch 839 are coupled to the patient 811 on the same side of the body of the patient 811. In such implementations, the second magnet 809 and the fourth magnet 837 each exert an attractive magnetic force on both the first magnet 807 and the second magnet 809. In some implementations, additional magnets are coupled to the first patch 805 and/or the second patch 839. In certain implementations, there may be more than two magnets coupled to the catheter 803 and/or more than two magnets coupled to the patient 811. In some implementations, there are multiple magnets coupled to the catheter 803 but only one magnet coupled to the patient 811. In some implementations, there are multiple magnets coupled to the patient 811 but only one magnet coupled to the catheter 803.

Figure 9:
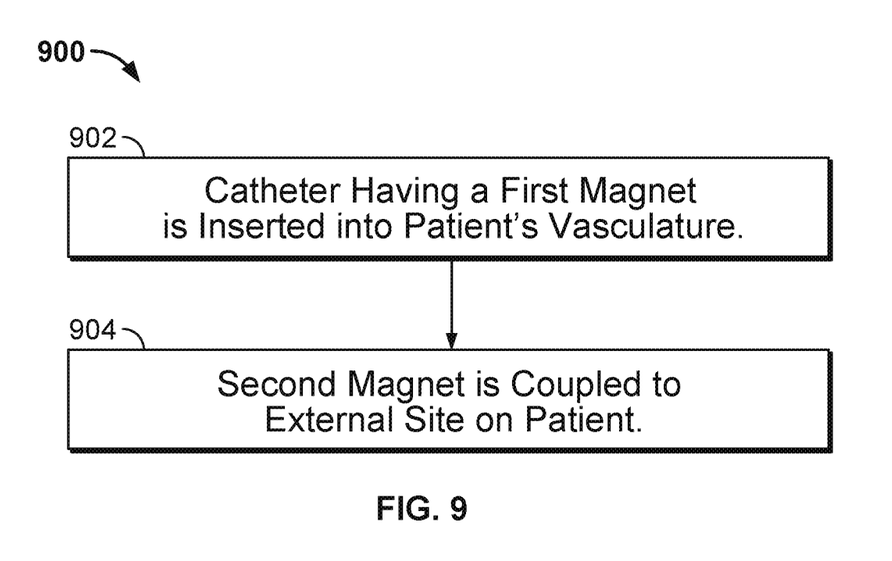
FIG. 9 is a flow diagram of an illustrative process for percutaneously inserting a catheter into a patient.

FIG. 9 is a flow diagram 900 of an illustrative process for percutaneously inserting a catheter into a patient. At step 902, the catheter (e.g., catheter 103 of FIG. 1) having a first magnet (e.g., first magnet 107 of FIG. 1) is inserted into a patient's vasculature. The first magnet may be coupled to a distal portion of the catheter. The catheter may include a heart pump disposed at an end portion of the catheter, and the first magnet is coupled to a distal end portion of the heart pump. The first magnet can be coupled to the catheter at a region proximal to the heart pump or distal to the heart pump. In some implementations, the surface area of the first magnet that is facing the patient's skin is 25 mm$^2$. During manufacturing, the first magnet may be coated, encased, enclosed, or hermetically sealed with an anti-corrosive layer, compound, or material (e.g., coated or encased with a biocompatible material/biocompatible metallic material such as stainless steel aluminum, gold, platinum, etc.). The catheter may be inserted through the femoral artery and advanced along the aorta until the pump is in a desired/optimal position (e.g., with the flexible atraumatic extension in the left ventricle away from anatomical structures and the outlet in the aorta, proximal to the aortic valve). The position of the pump can be monitored and confirmed using various imaging techniques, such as fluoroscopy. When the pump is in the desired position, medical personnel can fix the position of the pump in various ways. For example, a proximal portion of the catheter can be secured to or sutured onto the patient's leg near the insertion site and a tuohy borst valve can be actuated to prevent the catheter from sliding proximally or distally relative to a repositioning sheath and the insertion site.

At step 904, a second magnet (e.g., second magnet 109 of FIG. 1) is coupled to an external site on the patient such that the first magnet stabilizes the position of the catheter within the patient, relative to the second magnet. Coupling the second magnet to an external area of the patient the patient's skin can be accomplished using adhesive, such as adhesive that was coated onto the second magnet during its manufacturing phase. The second magnet may be included within a patch (e.g., patch 205 of FIG. 2) and the patch may be coupled to the patient's skin such as using adhesive coated onto the patch. In some implementations, the surface area of the second magnet that is in contact with the patient's skin is 25 mm$^2$.

The attractive force generated by the first and second magnets may be approximately equal to 2.5 N. In some implementations, the magnetic force is more than 2.5 N (e.g., 3 N, 5 N, 10 N, >10 N). In certain implementations, the magnetic force is less than 2.5 N (e.g., 2 N, 1 N, 0.5 N, 0.1 N).

If the first and second magnets are each sufficiently elongate (e.g., 1 mm, 2.5 mm, 5 mm, 7.5 mm, 10 mm, 50 mm, 10 cm, 30 cm, >30 cm), the first magnet and the second magnet may be used to cause the catheter to assume a preferred orientation within a plane (e.g., the coronal plane) of the patient. The length of the second magnet allows the second magnet to be attached to the skin of the patient within the coronal plane of the patient at a pre-determined angle relative to the patient's longitudinal axis. Similarly, the length of the first magnet allows the first magnet to be attached to the catheter at a pre-determined angle relative to the longitudinal axis of the catheter. Upon insertion of the catheter and the first magnet into the vasculature of the patient, the north and south poles of the first magnet and the south and north poles of the second magnet, respectively, will align. The pre-determined angles of the first and second magnets can be chosen such that upon alignment of the poles of the first and second magnets, the catheter assumes a certain angle relative to the patient's longitudinal axis within the patient's coronal plane. Similarly, the first magnet can include a first group of two or more spatially separated magnets, and the second magnet can include a second group of two or more spatially separated magnets. Torque can be applied to the catheter (e.g., in the coronal plane) by simultaneously applying oppositely direct forces to two magnets in the first group of magnets using the second group of magnets. This can also allow the catheter to be fixed in a preferred orientation relative to the patient's heart, blood vessels, and other surrounding anatomical features. For example, applying such a torque can change the rotational position of the flexible atraumatic extension relative to the coronal plane and relative to the patient's ventricle in order to avoid internal cardiac structures such as chordae and/or the mitral valve. As another example, if the distal portion includes one or more bends, during insertion of the device through the aorta and into the ventricle, the cannula and the flexible atraumatic extension may be angled toward a wall of the ventricle as shown in FIG. 10 in order to avoid the chordae and/or mitral valve.

Figure 10:
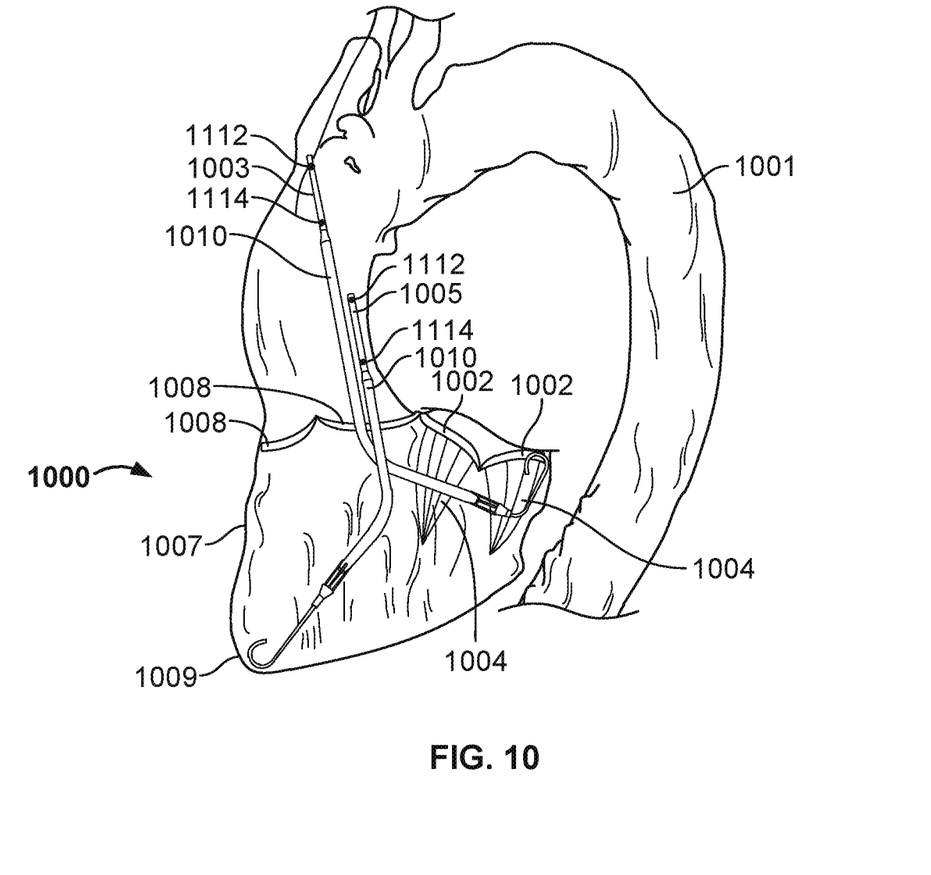
FIG. 10 is a cross section of a heart showing two rotational positions of a catheter within the heart.

FIG. 10 is a cross section of a heart 1000 showing two such rotational positions of a catheter within the heart 1000. FIG. 10 shows the heart 1000, the left ventricle 1007, the apex 1009 of the left ventricle 1007, the aorta 1001, the aortic valve 1008, the mitral valve 1002, the chordae 1004 of the mitral valve 1002, a first rotational position 1005 of a catheter 1010, and a second rotational position 1003 of the catheter 1010. The catheter 1010 includes magnets 1112 and 1114. In the first rotational position 1005, the catheter 1010 extends from the aorta 1001, through the aortic valve 1008, and into the left ventricle 1007. When the catheter 1010 is inserted down through the aorta in this orientation with the bend and the flexible atraumatic protrusion facing toward the mitral valve, the distal portion of the catheter 1010 such as the inlet ports and/or the protrusion may unintentionally contact the chordae 1004 of the mitral valve 1002. Inserting the catheter 1010 through the aorta in this first rotational position 1005 may be undesirable because contact with the chordae may complicate retraction of the catheter 1010 from the left ventricle 1007 and/or may interfere with or block the inlet port(s) of the catheter 1010, decreasing the amount of blood that can be pumped from the left ventricle into the aorta.

To avoid these challenges, a physician may use the magnets 1112 and 1114 to apply torque to the catheter 1010 to rotate the catheter 1010 from the first rotational position 1005 to a third rotational position (not shown) that is similar to the rotational position 1003, but will avoid contacting the chordae and mitral valve. This torque can be applied via external magnets (not shown), such as the second magnet 109 of FIG. 1. The distance separating the magnet 1112 from the magnet 1114 provides a sufficient lever arm for supplying the necessary torque. The lever arm may be 5 mm, 10 mm, 20 mm, 30 mm, 40 mm, 50 mm, 60 mm, 70 mm, 100 mm, 200 mm, or any suitable length. Although the magnets 1112 and 1114 are shown on the portion of the catheter 1010 located in the aorta, any suitable placement of the magnets 1112 and 1114 may be used. In some implementations, a single magnet can be used to provide the torque if it has a sufficient length for providing a lever arm (e.g., 3 mm, 5 mm, 10 mm, 20 mm, 50 mm, or any other suitable length). Thus, applying torque using magnets 1112 and 1114 can allow a user to rotate the catheter 1010 to a more desirable position to avoid anatomical structures such as the mitral valve and/or chordae.

Substantially fixating the position and/or orientation of the catheter can improve the effectiveness of the therapeutic and/or diagnostic procedures to which the catheter is directed. For example, substantially fixating a percutaneous catheter configured as a heart pump in its optimal position and orientation within the heart can improve cardiac assistance. Substantially fixating the position and orientation of the catheter may be especially beneficial for therapeutic or diagnostic procedures requiring a catheter to remain in a patient's vasculature for a long period of time, because the catheter would be less likely to stray from its optimal position and orientation.

The foregoing is merely illustrative of the principles of the disclosure, and the apparatuses and methods can be practiced by other than the described embodiments, which are presented for purposes of illustration and not of limitation. It is to be understood that the apparatuses and methods disclosed herein, while shown for use in percutaneously inserted catheters, may be applied to apparatuses and methods to be used in other types of therapeutic and diagnostic devices and methods.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

I claim:

1. A catheter apparatus comprising:
   a catheter;
   a heart pump coupled to a distal end portion of the catheter;
   a first magnet coupled to an exterior surface of the catheter;
   a second magnet configured to be coupled to a patient's skin;
   a third magnet coupled to a distal tip of the heart pump; and
   a fourth magnet configured to be coupled to the patient's skin at a position different from that of the second magnet;
   wherein the second magnet exerts a magnetic force on the first magnet, and the fourth magnet exerts a magnetic force on the third magnet such that the heart pump is stabilized relative to the second and fourth magnets when the catheter and the first and third magnets are positioned inside the patient's body,
   wherein the first, second, third and fourth magnets are spaced sufficiently far away from each other such that their magnetic fields do not interfere with each other and with operation of the heart pump, and
   wherein the distal tip of the heart pump is coupled to a flexible atraumatic extension.

2. The catheter apparatus of claim 1, wherein the atraumatic extension comprises a pigtail tip or a rounded tip.

3. The catheter apparatus of claim 1, wherein the third magnet is coupled to the distal tip of the heart pump via the flexible atraumatic extension.

* * * * *